(12) United States Patent
Darrach et al.

(10) Patent No.: US 7,332,345 B2
(45) Date of Patent: Feb. 19, 2008

(54) CHEMICAL SENSOR SYSTEM

(75) Inventors: Murray R. Darrach, Valencia, CA (US); Ara Chutjian, La Crescenta, CA (US)

(73) Assignee: California Institute of Technology, Pasadena, CA (US)

( * ) Notice: Subject to any disclaimer, the term of this patent is extended or adjusted under 35 U.S.C. 154(b) by 173 days.

(21) Appl. No.: 10/293,966

(22) Filed: Nov. 12, 2002

(65) Prior Publication Data

US 2005/0170523 A1  Aug. 4, 2005

Related U.S. Application Data

(63) Continuation-in-part of application No. 09/283,008, filed on Mar. 31, 1999, now abandoned, which is a continuation of application No. 09/235,046, filed on Jan. 20, 1999, now abandoned.

(60) Provisional application No. 60/072,179, filed on Jan. 22, 1998.

(51) Int. Cl.
  *H01J 49/04* (2006.01)
  *G06F 17/50* (2006.01)
  *G01N 33/22* (2006.01)
  *B01D 59/44* (2006.01)

(52) U.S. Cl. ............... 436/173; 250/281; 250/282; 250/288; 250/427; 436/96; 436/98; 436/104; 436/107; 436/110; 436/124; 703/13; 703/22

(58) Field of Classification Search ............... 250/281, 250/282, 288, 427; 436/173, 96, 98, 104, 436/107, 110, 124, 182; 703/13, 22
See application file for complete search history.

(56) References Cited

U.S. PATENT DOCUMENTS

| 4,649,278 A | 3/1987 | Chutjian et al. |
| 4,698,071 A | 10/1987 | Elias |
| 4,711,765 A | 12/1987 | Cates et al. |
| 4,814,613 A * | 3/1989 | Fite et al. ............ 250/292 |
| 4,933,551 A | 6/1990 | Bernius |
| 5,313,061 A | 5/1994 | Drew et al. |
| 5,374,828 A | 12/1994 | Boumsellek et al. |
| 5,459,315 A | 10/1995 | Waki |
| 6,300,625 B1 * | 10/2001 | Ishihara ............ 250/287 |

FOREIGN PATENT DOCUMENTS

| WO | WO 89/12315 | 12/1989 |
| WO | WO 89/12319 | 12/1989 |

OTHER PUBLICATIONS

Goddard, L. S. Proceedings of the Physical Sosiety 1944, 56, 372-378.*

(Continued)

*Primary Examiner*—Arlen Soderquist
(74) *Attorney, Agent, or Firm*—Fish & Richardson P.C.

(57) ABSTRACT

A chemical sensing apparatus and method for the detection of sub parts-per-trillion concentrations of molecules in a sample by optimizing electron utilization in the formation of negative ions is provided. A variety of media may be sampled including air, seawater, dry sediment, or undersea sediment. An electrostatic mirror is used to reduce the kinetic energy of an electron beam to zero or near-zero kinetic energy.

33 Claims, 5 Drawing Sheets

OTHER PUBLICATIONS

Henkelman, R. M. et al, Journal of Physics E: Scientific Instruments 1974, 7, 176-178.*
Fink, J. et al, Review of Scientific Instruments 1980, 51, 918-920.*
Kang, N. K. et al, Proceedings of the International Field Emission Symposium 1982, 29th, 101-110, Editors, Andren, H.-O. et al, Publisher: Almqvist & Wiksell, Stockholm, Sweden.*
Hermannsfeldt W. B. et al, AIP Conference Proceedings 1992, 260, 142-148.*
Chutjian, A. et al, Physical Reports 1996, 264, 393-470.*
Kelly, Ma. A. Journal of Electron Spectroscopy and Related Phenomena 1999, 98-99, 55-56.*
Reiche, s. Nuclear Instruments & Methods in Physics Research A 1999, 429, 243-248.*
Thompson, W. et al, Journal of Vacuum Science & Technology B 1983, 1, 1125-1128.*
Orient, O. J. et al, Review of Scientific Instruments 1985, 56, 69-72.*
Bielajew, A. F. et al, Nuclear Instruments & Methods in Physics Research 1987, B18, 165-181.*
Dahl, D. A. et al, Review of Scientific Instruments 1990, 61, 607-609.*
Kiss, L. et al, Nuclear Instruments and Methods in Physics Research B 1994, 85, 764-769.*
Komori, A. et al, Osaka Kogyo Daigaku Kiyo, Rikohen 1995, 40, 29-38.*
Kirstein, P. T. et al, Journal of Applied Physics 1958, 29, 1758-1767.*
Frobin, W., Optik 1968, 27, 203-212.*
Read, F. H., Journal of Physics E, Scientific Instruments 1969, 2, 165-169.*
Hoeper, P. S. et al, Journal of Applied Physics 1970, 41, 1879-1882.*
Ashley, J. R., Proceedings of the IEEE 1972, 60, 115-119.*
Shurn, P. J., International Electron Devices Meeting, (Technical digest), 1976, 523-526.*
Alton, G. D. et al, Nuclear Instruments & Methods 1980, 177, 273-280.*
Adachi, H. et al, Journal of Physics D, Applied Physics 1981, 41, 769-778.*
Kang, N. K. et al, Journal of Vacuum Science and Technology 1981, 19, 1077-1081.*
Kisker, E., Review of Scientific Instruments 1982, 53, 114-116.*
Hamarat, R. T. et al, Scanning 1984, 6, 75-79.*
Rempfer, G. F., Journal of Applied Physics 1990, 67, 6027-6040.*
Ishihara, M. et al, Nuclear Instruments & Methods in Physics Research 1992, B70, 445-450.*
Ximen, J. et al, Journal of Vacuum Science & Technology B 1993, 11, 275-280.*
Shishkin, G. V. et al, Journal of Mathematical Physics 1993, 34, 5037-5049.*
Colman, R. A. et al, Nuclear Instruments & Methods in Physics Research B 1994, 84, 515-520.*
Tiwari, T. et al, 1995 International Conference on Electromagnetic Interference and Compatibility (INCEMIC), Conference Proceedings (IEEE Cat. No. 95TH8121), 1995, 148-152.*
Wang, L. et al, Journal of Physics D: Applied Physics 1995, 28, 1791-1801.*
Kiss, L., Nuclear Instruments & Methods in Physics Research B 1996, 113, 71-74.*
Zhang, J.-J. et al, Fiber and Integrated Optics 2000, 19, 67-77.*
Casares, A. et al, International Journal of Mass Spectrometry 2001, 206, 267-273.*
J. Fernandez de la Mora et al., "Aerodynamic focusing of heavy molecules in seeded supersonic jets", *J. Chem. Phys.*, vol. 91, No. 4, pp. 2603-2615, Aug. 15, 1989.
L.E. Dejarme, et al., "Jet Separator/Membrane Introduction Mass Spectrometry for On-line Quantitation of Volatile Organic Compounds in Aqueous Solution", *Rapid Communications in Mass Spectrometry*, vol. 7, pp. 935-942, 1993.
Bruins, Developments in Interfacing Microbore High-Performance Liquid Chromatography with Mass Spectrometry (A Review), *Journal of chromatography*, vol. 323, pp. 99-111, 1985.
Kirby, et al., "A CE/ESI-MS Interface for Stable, Low-Flow Operation", *Anal. Chem.*, vol. 68, No. 24, pp. 4451-4457, Dec. 15, 1996.
Bernius, et al., "Pulsed, high-current, in-line reversal electron attachment detector", *J. Appl. Phys.*, vol. 66, No. 7, pp. 2783-2788, Oct. 1, 1989.
Bernius, et al., "Application of Reversal Electron Attachment for Ultrasensitive Detection of Thermal Electron-Attaching Molecules: CC14 and C6H5NO2", *Anal. Chem.*, vol. 62, No. 13, pp. 1345-1349, 1990.
Boumsellek, et al., "Increased Response of the Reversal Electron Attachment Detector and Modeling of Ion Space-charge Effects", *Anal. Chem.*, vol. 64, N. 18, pp. 2096-2100, Sep. 15, 1992.
Boumsellek, et al., "Negative-Ion Formation in the Explosives RDX, PETN, and TNT By Using the Reversal Electron Attachment Detection Technique", *J. Am. Soc. Mass Spectrom.*, vol. 3, pp. 243-247, 1992.
St.-Germain, "Volatile Organic Compound Analysis by an Inertial Spray Extraction Interface Coupled to an Ion Trap Mass Spectrometer", *Anal. Chem.*, vol. 67, No. 24, pp. 4536-4541, Dec. 15, 1994.
Kok, "Air Analysis Using Tenax Xollection with Jet-Separator Enrichment and Ion Trap Mass Spectrometric Analysis", *J. Am. Soc. Mass Sptrom.*, vol. 7, pp. 1172-1176, 1996.
Gordon, et al., "A Low-Energy Electron Source for Negative Ionization Experiments", *International Journal of Mass Spectrometry and Ion Processes*, vol. 72, pp. 285-297, 1986.
Tsuge, "Vacuum Nebulizing Interface for Direct Coupling of Micro-Liquid Chromatograph and Mass Spectrometer", *Analytical Chemisrty*, vol. 51, No. 1, pp. 166-169, Jan. 1979.
Yoshida, et al., "Improvement of Vacuum Nebulizing Interface for Direct Coupling Micro-Liquid Chromatograph with Mass Spectrometer and some application to Polar Natural Organic Compounds", *Fresenius Z Anal. Chem.*, vol. 311, pp. 674-680, 1982.
Yamashita, et al., "Electrospray Ion Source. Another Variation on the Free-Jet Theme", *J. Phys. Chem.*, vol. 88, No. 20, pp. 4451-4459, 1984.
Cohen, M., et al., "Effects of Azimuthal and Radial Angular Spread on E-beam Focusing Characteristics in the Presence of Space-charge Forces", *SPIE*, vol. 2013, pp. 24-42 (1993).
Edgcombe, C.J., "Sources of Velocity Spread in Electron Beams from Magnetron Injection Guns", *International Journal of Infrared and Millimeter Waves*, 16(1):83-87 (1995).
Hermannsfeldt, W.B., "Developments in Electron Gun Simulation", SLAC-PUB-6498, 26 pages, May 1994.
Hermannsfeldt, W.B., "Electron Trajectory Program", Report 1979, SLAC-226, 119 pages (1979).
Ishihara, M., et al., "A New Ray Tracing Code 'ELECTRA'", *Nuclear Instruments and Methods in Physics Research*, vol. B70, pp. 445-450 (1992).
Ko, K., et al., "Modeling Accelerator Structures and RF Components", *AIP Conf. Proc.*, vol. 297, pp. 1-8 (1994).
Munro, E., "Computer Programs for the Design and Optimization of Electron and Ion Beam Lithography Systems", *Nuclear Instruments and Methods in Physics Research*, vol. A258, pp. 443-461 (1987).
Ong, V., et al., "Why are Electron Capture Negative Ion Mass Spectra Not Reproducible? An Ion Source Problem", *J. of the Am. Soc. for Mass Spectrometry*, vol. 4, pp. 270-277 (1993).
Shakun, N.G., et al., "A System of Programs for the Evaluation of Charged Particle Trajectories in Electric and Magnetic Fields", *Izvestiya po Khimiya*, 22(3/4):584-585 (1989).
Tanabe, T., et al., "Computer Simulations on RIKEN Sub-millimeter FEL", *Reza Kagaku Kenkyu*, vol. 16, pp. 25-28 (1994).

* cited by examiner

CHEMICAL SENSOR SYSTEM

CROSS REFERENCE TO RELATED APPLICATIONS

This application is a continuation-in-part of U.S. patent application Ser. No. 09/283,008, filed Mar. 31, 1999 (now abandoned), which is a continuing application of U.S. patent application Ser. No. 09/235,046, filed Jan. 20, 1999 (now abandoned), which claims the benefit of the priority date of U.S. Provisional Application Ser. No. 60/072,179, filed on Jan. 22, 1998, which are incorporated herein by reference.

STATEMENT AS TO FEDERALLY SPONSORED RESEARCH

The subject matter described herein was made in the performance of work under a NASA contract, and is subject to the provisions of Public Law 96-517 (35 U.S.C. 202) in which the Contractor has elected to retain title.

BACKGROUND

This application relates to a method and apparatus useful in detecting minute quantities of a target molecule in a sample.

Detection of chemical particulates, contaminants, or vapors has important applications in public safety, national security and the security industry for detecting explosives and illegal drugs. Presence of such explosives, drugs, or chemical agents usually leaves a small amount of particles on surfaces, in the air, water, or sediment where the contraband is stored or handled. For example, particles of explosives or drugs on surfaces of luggage or clothes at airports or public buildings may lead to discovery of an attempted bombing or drug smuggling.

Techniques based on positive or negative ion formation via charge transfer to a target molecule (i.e., explosive constituent), or electron capture under multi-collision conditions in a Maxwellian distribution of electron energies (with a peak at about 40 millielectron volts (meV)) at the source temperature (300 K) have been developed. Such techniques include atmospheric sampling, glow-discharge ionization (ASGDI), atmospheric pressure ionization (API), electron capture detection (ECD) and negative-ion chemical ionization (NICI).

In order to maximize ion formation, and therefore target molecule detection sensitivity, high electron currents at low energies (<10 meV) were needed at the point of attachment between electrons and trace target molecules. To provide a better "match" between the electron energy distribution function and the attachment cross section, the electron reversal technique was developed. In this technique, electrons are brought to a momentary halt by reversing their direction with electrostatic fields. At a reversal region R, the electrons have zero or near-zero energy. A beam comprising target molecules is introduced, and the zero or near-zero energy electrons are attached to the molecules of the beam. Slowing the electrons to subthermal (<10 meV) energies is required because the cross section for attachment of several large classes of molecules (including the explosives, chlorohalocarbon compounds and perfluorinated carbon compounds) is known to increase to values larger than $10^{-12}$ cm$^2$ at near-zero electron energies. In fact, in the limit of zero energy, these cross sections are predicted to diverge as $\epsilon^{-1/2}$, where e is the electron energy.

This basic electron reversal technique has been improved upon to allow for better reversal geometry, higher electron currents, lower backgrounds and increased negative-ion extraction efficiency. See Bernius and Chutjian, U.S. Pat. No. 4,933,551; Boumsellek and Chutjian, U.S. Pat. No. 5,374,828, which are incorporated herein by reference.

In U.S. Pat. No. 4,933,551 ('551), the electron emitter was an indirectly heated oxide cathode with a planar (flat) surface geometry. The shapes of the emitter and mirror regions were used to calculate the fields-and-trajectories for the emitter region. The electron trajectories derived from this calculation were used to calculate the fields-and-trajectories for the reversal region. Subsequently, the trajectories were examined graphically. The mirror design was accepted if the incoming and reversed trajectories appeared to overlie each other in the graph. However, graphical examination of electron trajectories limits determination of the electron kinetic energy to no better than 20 meV. Furthermore, calculation of the electron trajectories was limited to a single pass through the electron optics lens stack. Since the reversed currents were not accounted for in the electron source region there was an inherent inaccuracy in the calculated electron trajectories from the cathode. These trajectories are affected by the space charge of the reverse current, but this effect was not taken into account in the '551 patent.

In contrast to the '551 patent, the electron source disclosed in U.S. Pat. No. 5,374,828 ('828) included a small "shim" electrode in the cathode region which created a mismatch between electron source and reversal equipotential configurations. The '828 patent disclosed a system that blended the spherical equipotentials adjacent to the emitter into the planar equipotentials of the reversal region. In contrast, the system disclosed in the '551 patent utilized planar equipotential surfaces both adjacent to the planar emitter and in the reversal region. The "shim" electrode disclosed in the '828 patent compensated for the differences in initial geometries by converting the spherical equipotentials at the cathode into planar equipotentials suitable for reversal within the planar equipotential configuration disclosed in the '551 patent. Essentially the spherical trajectories were "straightened out" into a parallel electric-field configuration which is not as precise as maintaining spherical equipotentials throughout the system.

Accordingly, in order to increase target molecule detection sensitivity, there exists a need to maximize ion formation in a reversal region of a device employing the electron reversal technique.

SUMMARY

A mechanism for matching the geometry of an electrostatic mirror at a reversal region to the geometry of an electron source, thereby increasing the quantity of low-energy electrons in a reversal region, is provided. This can be accomplished by analyzing the axial and radial kinetic energy of electrons at the reversal region and by maintaining a spherical equipotentials throughout the system. By matching the shape of the electron source with the reversal region, the invention provides a coupled system with enhanced ability to generate negative ions in the reversal region. The mechanism is useful for improving the ability of a chemical detector to detect a target molecule.

In one embodiment, a method for generating a negative ion in a reversal region is provided. The method includes providing an electron emitter having a spherically concave surface for generating an electron beam comprising electrons; providing a lens stack that includes 1) an electron extractor for electrostatically focusing the emitted electrons along an axes to a reversal region and 2) an electrostatic mirror for neutralizing the kinetic energy of the electrons. The method further includes determining the geometry of the lens stack; determining the fields and trajectories for the electrons comprising the electron beam by analytically determining the axial and radial kinetic energy of electrons at the electrostatic mirror, in which the trajectories of the electrons at the electrostatic mirror are calculated in a spherical electric-field configuration; determining the number of reflections made by the electron beam in the reversal region; comparing the results of the fields and trajectories determination with the number of reflections made by the electron beam results; modifying the lens stack according to the comparison such that an electron kinetic energy of 2 meV or less and at least 5 reflections at the reversal region are provided; and intersecting the reversal region with a target molecular gas beam comprising a target molecule, in which electrons attach to the target molecule and a negative ion is formed.

In another embodiment, an apparatus for generating low-energy electrons in a reversal region is provided. The apparatus includes an electron emitter having a spherically concave surface for generating an electron beam comprising electrons; a lens stack including 1) an electron extractor for electrostatically focusing the emitted electrons along an axes to a reversal region and 2) an electrostatic mirror for neutralizing the kinetic energy of the electrons. The apparatus further includes a means for determining the fields and trajectories for the electrons by analyzing the axial and radial kinetic energy of the electrons at the reversal region, in which the trajectories of the electrons at the reversal region are calculated in a spherical electric-field configuration; a means for determining the number of electron reversals in the reversal region; a means for comparing the results of the fields and trajectories determination with the number of electron reversals, and matching the geometry of the lens stack with the geometry of the electron emitter such that an electron kinetic energy of 2 meV or less and at least 5 reflections at the reversal region is provided.

In another embodiment, a chemical sensing apparatus for detecting the presence of a target molecule is provided. The apparatus includes a gas phase jet separator having at least one first wall adjacent to an injection port, a second wall proximal the injection port and a third wall distal the injection port; an electron-ion optic chamber in vapor communication with the jet separator, the chamber including 1) an electron emitter including a spherically concave surface; 2) a lens stack including i) an electron extractor for electrostatically focusing the emitted electrons along an axes to a reversal region; and ii) an electrostatic mirror for neutralizing the kinetic energy of the electrons. The chemical detection apparatus further includes a means for determining the fields and trajectories for the electrons comprising the electron beam by analytically determining the axial and radial kinetic energy of electrons at the electrostatic mirror, wherein the trajectories of the electrons at the electrostatic mirror are calculated in a spherical electric-field configuration; a means for determining the number of reflections made by the electron beam in the reversal region; a means for comparing the fields and trajectories with the number of electron reflections and modifying the lens stack to provide an electron kinetic energy of 2 meV or less and at least 5 reflections at the reversal region; an ion extraction component in ion communication with the reversal region; and a mass analyzer in ion communication with the extraction component.

In another embodiment, a device for inhibiting deposition of a non-conductive substance on the inner surface of an electrostatic analyzer is provided. The device includes a non-solid material covering an aperture integrally-associated with the electrostatic analyzer. The aperture is in the direct line of sight of an electron emitter. The device substantially maintains the integrity of an electrostatic field and permits the flow of negative ions through the electrostatic analyzer while presenting a decreased surface area for the deposition of non-conductive material.

In yet another embodiment, a method for inhibiting deposition of a non-conductive substance on the inner surface of an electrostatic analyzer is provided. The method includes contacting a non-solid material covering an aperture integrally-associated with the electrostatic analyzer with positive ions and negative ions. The aperture is in the line of sight of an electron emitter and the material substantially maintains the integrity of an electrostatic field and permits the flow of negative ions through the electrostatic analyzer.

The methods, apparatuses and devices described herein can be integrated into specific extraction and chemical separation techniques. For example, in the case of explosive residues present in water or on sediment, a vapor including a target molecule can be extracted from sediment or the sea water using a solid-phase microextraction fiber. The explosive residues including a target molecule can be desorbed by heating the fiber in a chamber or oven and further processed in a jet separator where the residue components are separated from background air or carrier gas by supersonic expansion. The sample molecules are then transported to an electron-ion optic system including an electron source, such as a cathode, which emits electrons toward an electrostatic mirror. The electrostatic mirror provides an electrostatic field to stop the electrons and reflect them. This reduces or neutralizes the kinetic energy of the electrons to zero or near zero, at which energy they efficiently attach to a target molecule generating negative ions which are then transported into a mass spectrometer and analyzed.

The details of one or more embodiments of the invention are set forth in the accompanying drawings and the description below. Other features, objects, and advantages of the invention will be apparent from the description and drawings, and from the claims.

DRAWING DESCRIPTIONS

These and other aspects will now be described in detail with reference to the accompanying drawings, in which:

FIG. 1 depicts a schematic diagram of a system for detecting target molecules.

FIG. 2 depicts a schematic representation of an electron-ion optic system. Shown are the spherical cathode component (F, V1, V1'), reversal component (V2, V2'), and ion extraction component (V3, V4). The negative ions are deflected 90° by the electrostatic analyzer (ESA) and into the quadrupole mass spectrometer (QMS). Lens element voltages are cycled by fast MOSFET switches (S1-S4) controlled by a master clock. The asterisk (*) on the ESA outer sphere denotes the area which is in direct line-of-sight of the emitter F.

DETAILED DESCRIPTION

Figure 1:
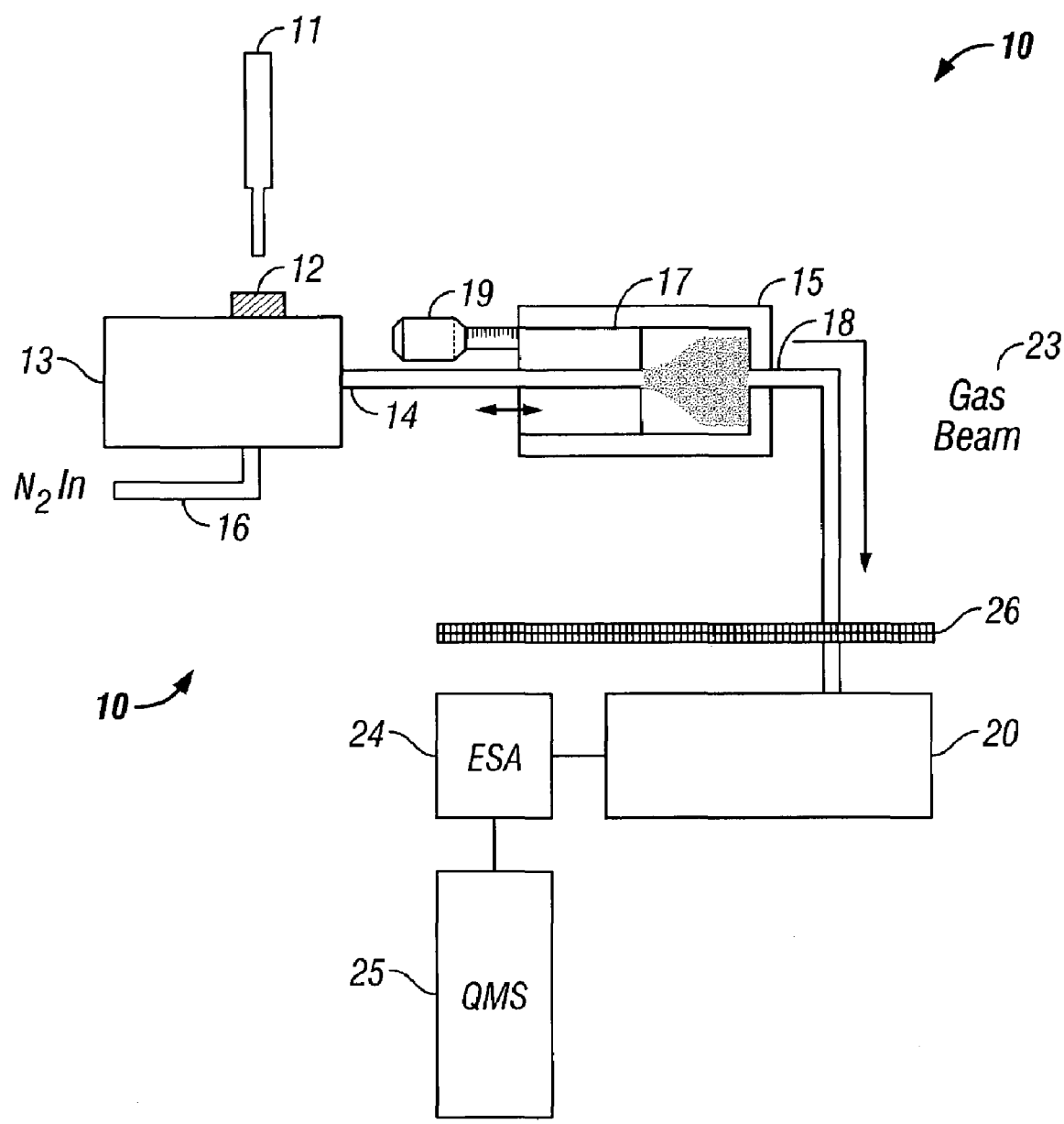

The methods, apparatuses and devices described herein have applicability to the detection of a broad range of chemicals of interest. These include, for example, chemicals associated with explosives and their manufacture, including unexploded under-water ordinance, explosives or chemicals in waste water from industrial or military areas, detection of toxic substances produced by manufacturing plants, and detection of nerve and blister agents. Such applicability has utility in protecting buildings, harbors, embassies, airports and personnel against such chemical dangers, including terrorist activity.

In the present invention, the reversal region R is matched to the shape of the electron emitter using a three-dimensional fields-and-trajectories calculation with full accounting of electron and ion space charge. "Matched," as used herein, means that the shape of the electrostatic field at the reversal region is adjusted to increase the number of electrons reflected back to the cathode with the electrons having a low axial and radial energy. Increasing the number of reflected electrons in the reversal region increases the opportunities for ion formation of a target molecule. In this regard, an increase in detection sensitivity for classes of zero electron-energy attaching molecules, including explosives, is provided.

This ionizer system comprises a source of electrons, which may be from a directly or indirectly-heated cathode, or a field-emission source. An electron optics lens system extracts and focuses the electron beam onto an electrostatic mirror which slows the electrons contained in the beam to zero- or near-zero electron energies. Each band of energies from the cathode source will be stopped at a different plane in this mirror thereby providing a plurality of stacked planes of zero-energy electrons. The target gas beam comprising a target molecule is introduced at this region, and the zero or near zero velocity electrons will attach to the target molecule and form a characteristic negative-ion spectrum ("fingerprint") of the target molecule which is analyzed by a subsequent mass spectrometer.

The method and apparatus are particularly useful for detecting target molecules that possess a large efficiency (cross section) for attaching the zero-energy electrons. As used herein a "target molecule" includes chemicals such as explosives including RDX, TNT, PETN and EGDN. Target molecules further include nerve agents such as Tabun (GA), Sarin (GB), Soman (GD), GF, V-agent (VX) (phosphonothioic acid, methyl-, S-(2bis(1-methylethylamino)ethyl)O-ethyl ester) and pyridostigmine. Target molecules further include pulmonary intoxicants such as phosgene (CG), diphosgene (DP), chlorine, and chloropicrin (PS), blood agents such as cyanide and vesicants or blister agents such as sulfur mustard (H/HD) and nitrogen mustard (HN), arsenicals (lewisite (L)), and phosgene oxime (CX). Incapacitating agents such as BZ. Target molecules further include blood agents such as hydrogen cyanide (AC) and cyanogen chloride (CK) and riot control agents such as mace or pepper spray. Target molecules also include electronegative vapors associated with plastic explosives. Such target molecules are detected in parts-per-trillion (pptr) amounts and less. Accordingly, the method and apparatus are useful for detecting explosives, chemical warfare agents, and contraband. Separate interfaces are provided for detection of air or water-borne trace chemicals, or trace chemicals in dry or undersea sediment.

If the target molecule prefers to attach a higher-energy electron, then the electrostatic potential on the mirror electrode is weakened, so that a higher-energy electron beam passes through the electron attachment region, and attachment occurs at those energies. The electron attachment and ion extraction are carried out in a pulsed mode: the electron beam is pulsed "on," attachment takes place, the electron beam is pulsed "off," and the subsequent ion optics are pulsed "on" to extract and focus the negative ions onto the entrance aperture of the mass analyzer. This analyzer can be of any type adequate to provide the needed mass range and resolution. This includes, but is not limited to, a quadrupole, ion-trap, magnetic sector, time-of-flight, or trochoidal analyzer. Miniaturization of the entire system is also feasible, and is considered part of the present application. The attachment cross section of an explosive is known to be large at zero electron energy and almost certainly have an "s-wave" dependence in which the attachment cross section is proportional to $\epsilon^{-1}$ (where $\epsilon$ is the electron energy). Hence, utilization of target, and optimization of the formation of the negative ions is provided.

In general, explosive molecules have an extremely large cross section for attaching zero-energy electrons. This cross section varies as (electron velocity)$^{-1}$. Hence, the attachment rate (or ionization efficiency) is favored for slow electrons. For molecules which attach higher-energy electrons, the mirror can be weakened to generate faster electrons at the point of attachment to a target molecule.

Referring to FIG. 1, a sensor apparatus 10 for analysis of trace chemicals is shown. In one embodiment, the trace molecules are thermally desorbed from the solid-phase microextraction (SPME) fiber 11 after injection through septum 12 into an oven 13. The oven heats the sample sufficiently to vaporize the sample. The vapors pass through the gas line 14 into the adjustable jet separator 15. Nitrogen gas, preferably pure nitrogen, at approximately 1 p.s.i. flows through the gas inlet 16 and oven 13. The nitrogen gas carries the trace chemicals through the gas line 14 and the source orifice 17 of the jet separator 15. The spacing between the source orifice 17 and skimmer orifice 18 can be adjusted for maximum focusing of the mass peak of interest. The distance is adjusted to allow for supersonic expansion from the source orifice to provide separation of the heavy molecular weight species from nitrogen in the jet separator.

The desorption oven 13, gas line 14 and jet separator 15 can be made of any material capable of withstanding the temperature and forces applied and which does not produce interferant vapors or cause loss of analyte vapors due to adsorption. Such materials can include titanium and stainless steel. In a preferred embodiment, the oven, gas line and jet separator are made of stainless steel. In another preferred embodiment, the jet separator is glass-lined. The oven and gas line are typically maintained at 190° C. and the jet separator at 140° C. during operation, however, these temperatures can be adjusted depending upon the chemical being analyzed.

An adjustment member 19 (micrometer screw) is in adjustable communication with at least one wall of the jet separator and allows for the modification of the distance between the source orifice 17 and skimmer orifice 18, such that the skimmer-nozzle distance in the jet separator can be adjusted. The distance can be adjusted depending upon the chemical or sample being analyzed and the carrier gas being used. The supersonic expansion results as the gas vapors flow from a higher pressure region into a region of significantly lower pressure through the nozzle opening. When the nozzle diameter is much larger than the mean-free path of the molecules or ions, the molecules or ions enter the lower pressure region forming a supersonic jet. The ions or molecules in the supersonic jet have a statistical average direction or axis of flow. The supersonic expansion in the jet causes a narrowing in the energy distribution of the molecules and ions in the jet. As the ions expand through the small orifice, their internal and kinetic energies are shared through two-body collisions, and their energies become more equalized.

The gas beam 23 is introduced into a sensor ionizer, also referred to as an electron-ion optic system 20, such that the target molecules in the gas stream contact a low energy electron beam in the optic system 20. The gas beam 23 may be injected parallel or perpendicular to the electron beam for maximum target-electron overlap. With reference to FIG. 1, the electrons contact the target gas beam 23, which may contain a target molecule (e.g., explosive molecules). Negative ions may be formed by the electron dissociative attachment process.

The READ is a pulsed device and in the first half of the cycle electrons are reflected in the electrostatic mirror and negative ions are formed in the attachment region. In the second half of the cycle, the negative ions are extracted from the attachment region and in the current embodiment are focused into an electrostatic analyzer (ESA) 24 and then into a quadrupole mass spectrometer (QMS) 25. The electron-ion optics system 20, the ESA 24, and mass analyzer 25 may be enclosed in a vacuum chamber 26.

Any type of mass analyzer may be adapted to the present invention, including variable dispersion mass spectrometer as described in PCT publication number WO89/12315, time-of-flight mass spectrometers, magnetic sector mass spectrometers, ion trap, and quadrupole mass spectrometer, to name but a few. The quadrupole mass analyzer (QMS) 25 typically comprises four rod electrodes placed in parallel to and symmetrically around a center axis with a pair of non-conductive holders for holding the electrodes at both ends of the four rod electrodes and a pair of plates for clamping the non-conductive holders (see for example, U.S. Pat. No. 5,459,315).

The mass spectrum of the negative ions is a unique fingerprint of the particular species present in the starting sample. Due to the potentials applied to the lens elements in the first half of the READ cycle, positive ions formed in the attachment region are extracted and focused into the electrostatic analyzer (ESA) 24, which deflects them away from entering the mass spectrometer. The ESA therefore provides a method to differentiate the negative and positive ions produced in the READ. If the positive and negative ions are not differentiated the mass spectrum will no longer be a unique fingerprint of the species of interest.

It is noted that positive and negative ions can be differentiated without the use of an ESA. For example, differentiation can be based upon the arrival times of the ions in the mass spectrometer. Negative ions are focused into the mass spectrometer only in the second half of the READ cycle, while positive ions appear during the first half. By excluding data collection during the second half of the cycle the uniqueness of the negative ion mass spectrum can be preserved.

Figure 2:
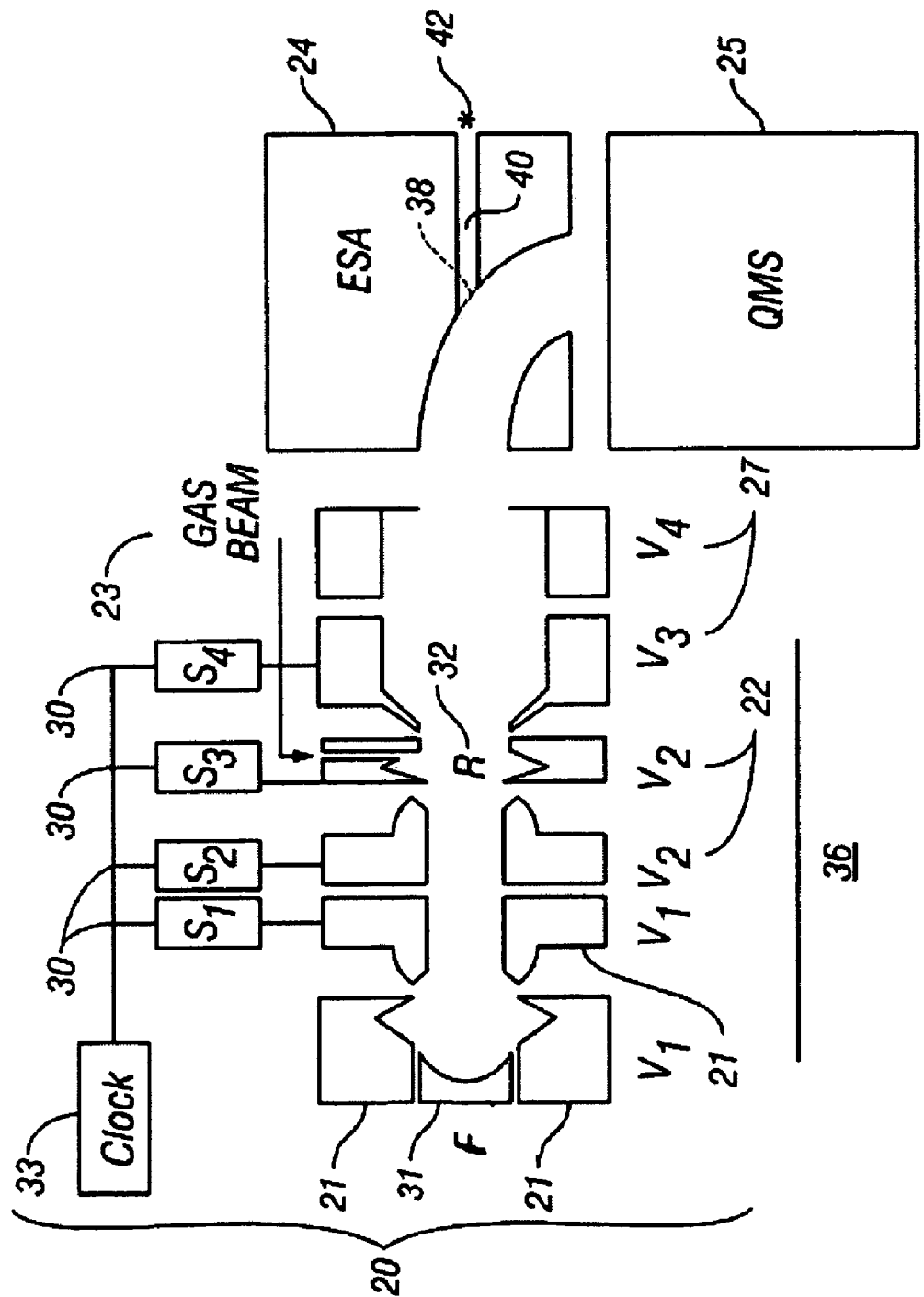

Referring to FIG. 2, the electron-ion optic system 20 includes a spherical cathode and electron extractor component (F, V1, V1') 21, a reversal component (V2, V2', V3) 22, an ion extraction component (V2, V2', V3, V4) 27, MOSFET switches (S1-S4) 30 and a clock controlling the MOSFET switches 33. The MOSFET switches are operationally associated with the spherical cathode component 21, the reversal component 22 and the ion extraction component 27. The spherical cathode component 21 includes an electron emitter (F) 31 such as a directly-heated cathode or indirectly-heated oxide dispenser cathode. The electron source (i.e., electron emitter or cathode) 31 emits electrons that are focused into the reversal component 22. A "spherical cathode," as used herein, is defined as a cathode having a concave surface for emitting electrons that is part of a hemisphere. The design of the electron emitter can include the use Child's Law to determine the width of the spherical cathode. The concave face of the cathode can be designed with a radius of curvature r such that 2r is greater than that width. While decreasing the radius of curvature to half the cathode width will result in a true hemispherical surface for maximum electron emission, electrons emitted near the edge of the hemisphere will have an initial direction of motion perpendicular to the axis of the focusing and accelerating lens elements, which will tend to interfere with the desired shape of the beam being formed.

The reversal component functions as an electrostatic mirror to reduce or neutralize the kinetic energy of the electrons at the reversal (R) position 32. The reversal component is comprised of electrodes that create electric fields. The electric fields act as lenses which modify electron velocity by reducing it to zero or near zero. The electrodes V2 and V2' comprising the reversal component may be a conductive metal or any material suitable for such use. The electron source and reversal component comprise the lens stack 36. The geometry of the elements comprising the lens stack are shaped to provide a reversal region that is matched to the shape of the spherical electron emitter. This is accomplished by analyzing electron trajectories at the equipotential surfaces of the reversal component. In contrast to previous methods, the spherical equipotentials at the cathode of the present method are not converted into planar equipotentials by straightening them into parallel electric-field configurations. In the present system, spherical potentials are maintained throughout the system (i.e., from cathode to reversal region). Fields and trajectories are computed using a three-dimensional fields-and-trajectories calculation with full accounting of electron and ion space charge. Typically the calculation is a component of computer code. The quality of the reversed electrons at the position R, i.e., how close their velocity in the radial and axial directions is reduced to zero, is monitored as a function of lens stack geometries which includes lens positions, lens shapes, and the degree of space charge in the electron beam. The monitoring is accomplished by querying the computer code for these quantities at the location R.

The electron beam is square-wave modulated by fast switches $S_1$-$S_4$ with a nearly 50% duty cycle. These switches are power MOSFET-based to ensure fast (50 ns) rise times between full-floating lens voltage. Electron attachment to the sample molecules takes place at the reversal plane R during one half of the duty cycle when the electron beam is "ON". The resulting negative ions are extracted during the second half of the duty cycle (electron beam is "OFF") and focused by ion extraction component (V2, V2', V3, V4) 27 onto the entrance plane (W1) of a electrostatic analyzer (ESA) 24. The extracted ions are then deflected by the ESA to insure the sign of charge, and further focused onto the entrance plane (W2) of a quadrupole mass analyzer (QMS) 25.

Electrons are generated at the electrode F and accelerated into the reversal region R where attachment or dissociative attachment (DA) to sample molecules takes place. Fast switches $S_1$-$S_4$ pulse electrons on during one-half cycle, then pulse negative ions out towards the electrostatic analyzer 24 during the second half. Ions selected by the ESA are focused into the QMS and individual masses are detected.

In another embodiment, a device for shielding the entrance to aperture 40 contained within ESA 24 is provided. As previously noted, an apparatus of the invention includes an electrostatic analyzer (ESA) 24. The ESA provides a means of differentiating negative and positive ions by acting as an electron energy filter. Such filter may be any electrostatic or electromagnetic energy analyzer configured for the present application, for example being a cylindrical electrostatic analyzer, or a hemispherical electrostatic analyzer.

Figure 3A:
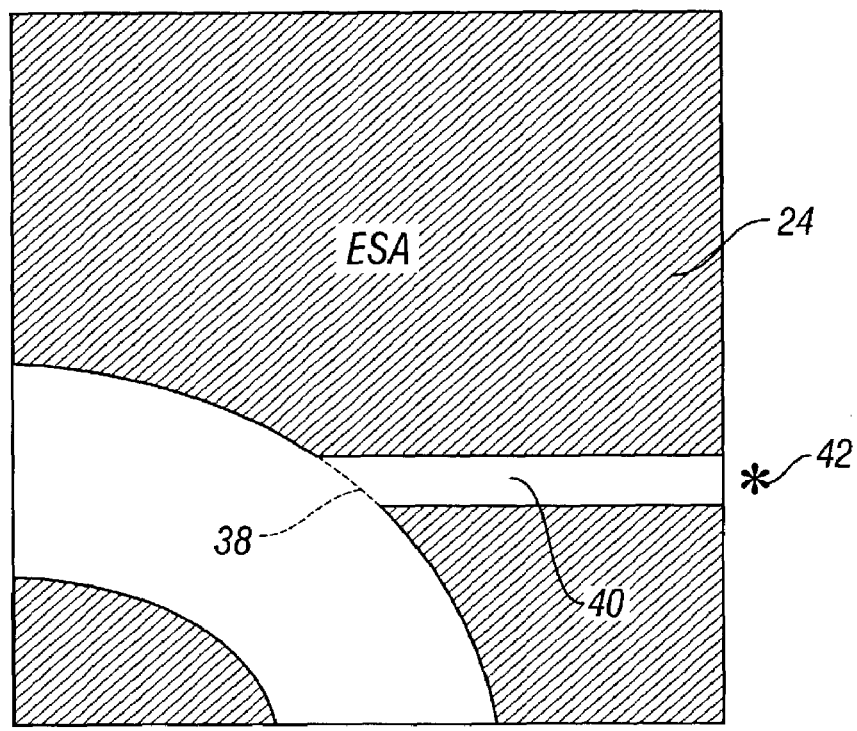
FIG. 3A and FIG. 3B depict enhanced views of the ESA outer sphere and the aperture located in direct line-of-sight of the emitter F. A device that maintains the integrity of the electric field shields (covers) the aperture and inhibits the deposition of non-conductive substances.
Figure 3B:
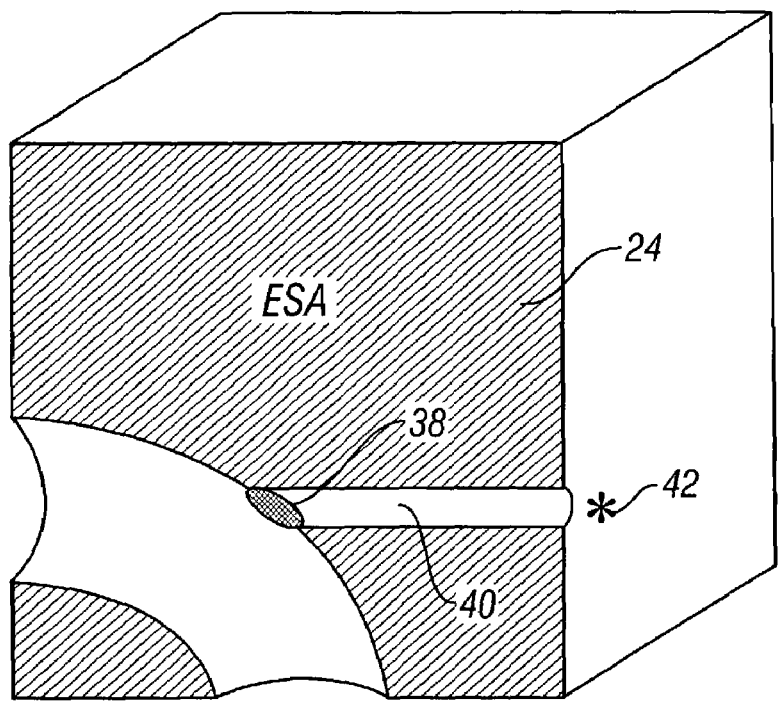

Negative ions formed at the reversal region are focused onto the ESA 24. However, due to the potentials applied to the lens elements in the first half of the READ cycle, positive ions formed in the attachment region are extracted and focused into the ESA 24 as well. The ESA generally deflects the unwanted positive ions away from entering the mass spectrometer. Referring generally to FIG. 3A and FIG. 3B, the present studies have determined that the outer surface of the ESA at position 38, which is in the line-of-sight of the electron emitter F, is susceptible to contamination with non-conductive material. The non-conductive material results from the decomposition of the chemical constituents present in the sample. Such decomposition is attributable to charging of the outer radius of the ESA elements by positive ions.

In order to reduce the surface-charging effects of the ESA and inhibit the deposition of non-conductive contaminants within the apparatus, a device 38 (FIG. 3A and FIG. 3B) which resides on the outer sphere of the ESA and is in the direct line-of-sight of the electron emitter F, is provided. The device 38, while maintaining the integrity of the electrostatic field, presents a reduced surface area at the critical region of the ESA most susceptible to contamination. The device is composed of any material that shields the entrance to the aperture 40 but does not disrupt the passage of negative ions through the ESA 24. Further, the device is composed of any material that does not completely prevent the egress of positive ions from the ESA through aperture 40. The device is positioned at the entrance of aperture 40. Aperture 40 provides a channel integrally-associated with the ESA through which positive ions exit the ESA. The device can be removable or non-removable from the ESA.

A device 38 positioned at the entrance of aperture 40 can be a mesh, screen, membrane or any porous material that provides a plurality openings forming a non-solid surface at a critical region 42 located on the outer sphere of the ESA and in the direct line-of-sight of the electron emitter F. The device will present less than 100% solid surface area in the critical region. For example, the device can present about 10% of a solid surface area at the critical region, thus reducing by about 90% the material to be coated by contaminants. It is understood that any amount of solid surface which is less than 100% solid at the indicated position and is sufficient to maintain the integrity of the ESA electrostatic field is encompassed by the present invention.

Figure 4:
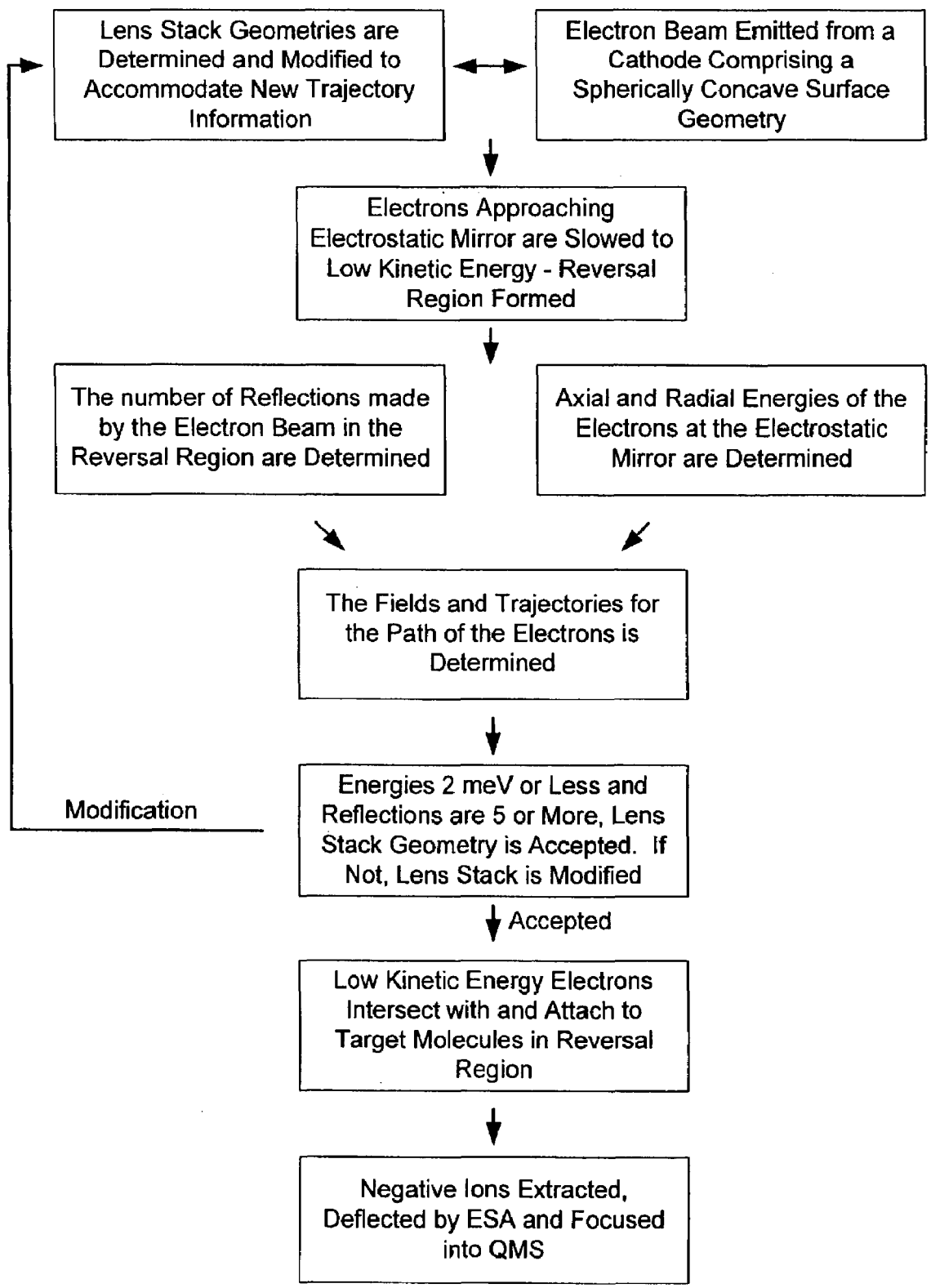
FIG. 4 depicts a flow diagram of an exemplary method for detecting a target molecule.

Referring generally to FIG. 4, lens stack geometries are initially determined and subsequently modified to accommodate electron trajectory information so that electron reversals are matched to the electron emissions. The electron trajectory can be determined analytically from the results of the axial and radial kinetic energies of the electrons at the reversal region R. The axial and radial electron kinetic energies are obtained from the computation itself. Alternatively, the electron trajectories can be examined visually by specifically noting the number of reflections the electron beam makes in the reversal region. If the electron energies calculated at the reversal region R are less than 2 meV, and the number of reflections the electron beam makes in the reversal region is more than 5, then the geometry of the lens stack is accepted as optimized. The entire lens stack geometry can be matched to the spherically concave electron emitter geometry. Thus, the entire lens geometry is considered during the computer fields and trajectories analysis.

The lens stack geometry (i.e., the shape and positions of the elements comprising the lens stack) is initially determined and subsequently modified so that it is matched to the geometry of the electron emitter.

The space-charge distribution of the electron beam and lens geometries can be determined by calculations or computer codes. A means for determining the fields and trajectories for the electrons in a spherical electric-field configuration includes any means known to the skilled artisan. For example, the Herrmannsfeldt field and trajectory code can be used to calculate electron trajectories. Additional codes include, but are not limited to, the MEBS code (Munro Electron Beam Software), MAFIA code and VECTOR FIELDS code.

As the electrons approach the reversal region, they are slowed and their kinetic energy is reduced to a few millielectron volts. Their energy becomes almost entirely potential energy. Sample molecules are passed through the region of low energy electrons. Accordingly, electrons emitted from electron source 31 having a particular energy are decelerated by the reversal component (i.e., electrostatic mirror) 22 to a zero, or near zero, longitudinal and radial velocity at the reversal plane. The electrons emitted from the electron source have a Boltzman distribution of kinetic energy with a mean energy of about 0.25 electron volts. The region of electron reversals at the electrostatic mirror is comprised of a spatial extent of stacked reversal planes along the axis of the lens system. For example, the electrons with low kinetic energy will reverse before those electrons with higher kinetic energy.

The electrostatic mirror is designed to facilitate an intersection between the spatial extent of the reversal planes and the spatial extent of the target molecular gas beam, thereby providing enhanced spatial overlap between the slowed or stopped electrons and the target molecules. The enhanced spatial overlap increases the efficiency of electron attachment to the target molecules. Therefore, an electrostatic mirror of the invention is designed to avoid placing large voltage potentials on the electrostatic mirror because a sharp reversal region will form. This sharp reversal region will be spatially-narrow in extent such that a less than optimal spatial overlap with the target beam will occur. Similarly, the electrostatic mirror is designed to avoid low voltage potentials on the electrostatic mirror. Such potentials spread the reversal planes out in space which encourages 1) poor reversals packets for high electron currents (packets are of too high a radial energy), and 2) larger planes in a spatial extent than the target beam, hence providing less than optimal overlap or ionization efficiency.

Subsequent to reversal at the electrostatic mirror, the electrons which did not undergo attachment to a target molecule present in the gas beam are reflected backwards, and travel in the opposite direction through the electrostatic lens systems. The present apparatus provides a mechanism for confining and focusing these "backward" trajectories such that their effect is included in the trajectories of the forward-going electron trajectories entering the reversal region.

The geometries of the spherical cathode component and of the lens stack are communicated to a computer comprising software. The software optimizes the geometry of the lens stack with respect to the spherical cathode component. Modifications in the electron emission profile necessitates a modification in the geometries of the components of the lens stack in order to enhance the interaction between electrons with low kinetic energy and the target molecules present in the gas beam which traverse the reversal region (R) (FIG. 1 and FIG. 2, 32). Electron paths are calculated in a spherical electric-field configuration (i.e., as spherical equipotentials). In contrast to previous chemical detection systems, spherical trajectories are not linearized into a parallel electric-field configurations. Thus, an means to more precisely identify the quantity of electron reversals occurring in the reversal region is provided.

Previous attempts to calculate the trajectories of electrons in an electron reversal system have been limited. Such attempts generally divided the calculations into sections. For example, in U.S. Pat. No. 5,374,828 ('828), electron trajectories were calculated by dividing the system into two parts: part 1 included the electrodes 11, 11', 12, 13, 14; and part 2 the electrodes 12-17 (see FIG. 1 of the '828 patent). Three electrodes 13-15 were made common to both parts so that fringing fields from part 1 were included in part 2. After determining the electron trajectories for part 1, the output trajectories were injected (as initial conditions) into part 2 at a position on the lens axis where the potential was identical in both parts. While adequate, the partitioning electron trajectories and subsequently piecing them back together is inherently less precise than the method presented herein.

Thus, the geometry of the elements comprising the lens stack are shaped to provide a reversal region that is matched to the shape of the spherical electron emitter. The small spherically-shaped tips on lens elements V1 and V2 (see FIG. 2, 21 and 22) are examples of how the lens stack can be optimized to accommodate the spherical extraction technique by analyzing electron trajectories at the equipotential surfaces of the reversal component. Once the initial analysis is complete, the lens stack is modified to match the geometry of the electron source. As previously noted, the geometries of the elements of the lens stack are optimized with respect to the electron emitter. The optimization is concurrent because any modification in the electron emission profile necessitates a modification in the shape of the mirror. The two portions of the electrostatic lens systems, the electron source and the electrostatic mirror, comprise a coupled system. Optimum attachment efficiency of the systems arises from ensuring that there are multiple passes of the electron beam between the reversal region and the cathode. The effect is to maximize the number of electron transits at the highest electron current through the target beam. The invention provides an apparatus and method for coupling an electron source with a lens system comprising an electrostatic mirror. The electron source and lens system are concurrently modulated such that fields-and-trajectories codes are not limited to modeling only the trajectory a single packet of electron current emitted from the electron source. Accordingly, multiple reversals are observed in the code as a segment of electron charge shuttling between the cathode and reversal regions of the coupled lens systems.

For example, referring generally to FIG. 2, the electron source 31 can comprise a directly-heated, spherical cathode from which electrons are extracted and accelerated by a lens system. They are then focused into an electrostatic mirror. The mirror decelerates the electron beam to zero longitudinal velocity and near-zero radial velocity at the reversal plane R. At R, the reversed electron beam crosses or "intersects" the molecular target beam. Negative ions formed at R by the attachment or dissociative attachment (DA) process are then extracted by elements V3 and V4.

The physical description of the computer simulation is that of a coupled lens system focusing and reversing continuously-emitted electron current over a distinct period of time. The design of the optical system ensures that high quality reversals are still affected with the inclusion of successive electrons being injected into the system.

EXAMPLE

Sediment suspected of containing trace amounts of explosive material were extracted using various techniques. In one technique a solid-phase extraction (SPE) was used, in another technique a salting-out solvent extraction was used, and in yet another technique membrane SPE was used. For the present investigation the extraction of explosives from the aqueous solution was effected by solid phase microextraction (SPME). SPME has been successfully integrated to various sensor technologies, such as gas chromatography and high performance liquid chromatography. A poly(dimethylsiloxane)divinylbenzene (PS-DVB) fiber was used and found to have the highest relative efficiency of the commercially available fibers for TNT extraction.

Figure 5:
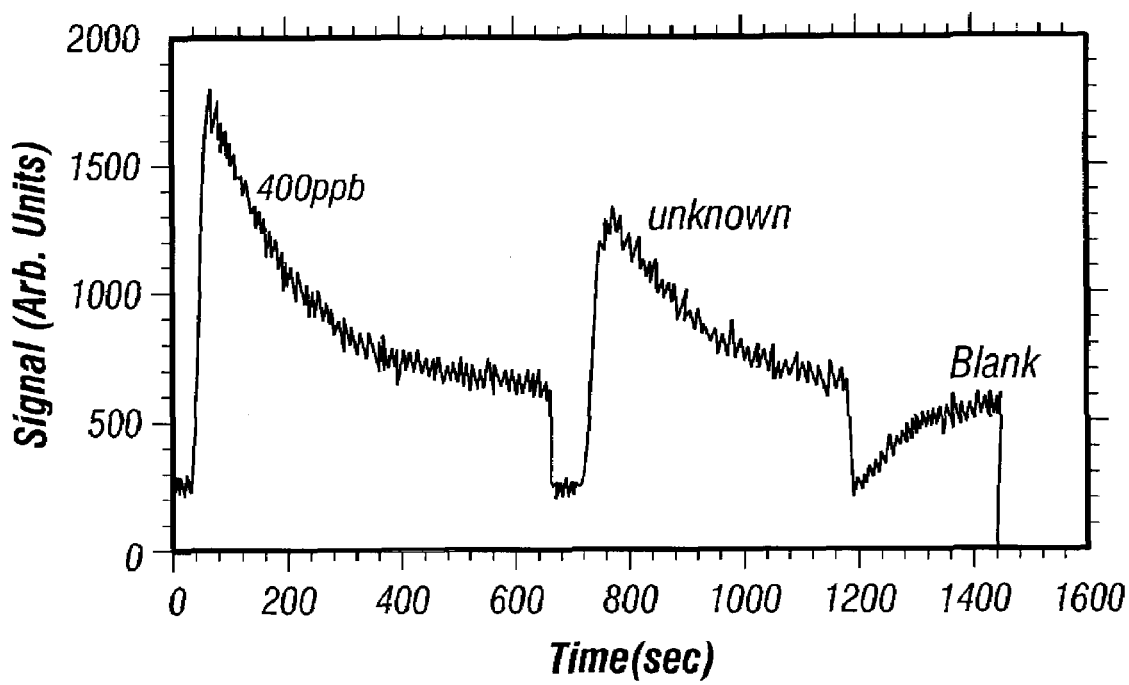
FIG. 5 depict a display of the TNT negative-ion fragment signal at a mass (m) to a charge (e) ratio (m/e) of 167 u. Time is shown after injection of extractions from a 400 ppb standard TNT solution, a sediment-extraction sample of unknown concentration, and a blank.

Thermal desorption of explosives from the SPME fiber should be performed at a high temperature, suggested to be slightly above the boiling point of the analyte. Shown in FIG. 5 is the time evolution of the fiber desorption. The mass negative-ion peak m/e=167 of TNT is monitored. At this oven temperature (approximately 190° C.), the desorption process takes from 1 to 2 min. Results with a blank extraction is also shown in FIG. 5. The slow rise in background level after injection of the blank sample is due to the rise in the READ chamber pressure from $8 \times 10^{-6}$ to $1.4 \times 10^{-5}$ Torr. Typically, an SPME extraction of a sediment sample is sequentially analyzed with SPME extractions of a spiked sample of known TNT concentration, and then a seawater blank.

Figure 6:
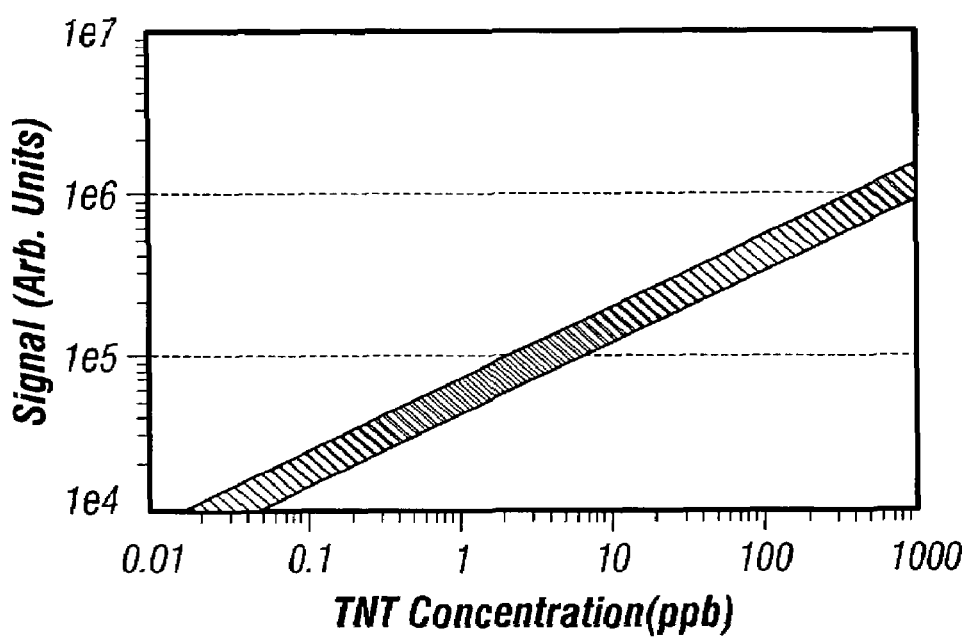
FIG. 6 depicts a sensitivity curve of a mass spectrometry system to TNT concentration in water (m/e=167 u monitored) The shaded region represents the sensitivity, and its error, in determining the TNT concentration corresponding to the indicated signals.

During the 1-2 mm the explosives were desorbing from the fiber the quadrupole mass spectrometer could be tuned to various mass peaks of the fragmentation pattern, mapping out the characteristic dissociative attachment fingerprint. FIG. 6 depicts a sensitivity curve of a mass spectrometry system to TNT concentration in water (m/e=167 u monitored). The shaded region represents the sensitivity, and its error, in determining the TNT concentration corresponding to the indicated signals. If ions with m/e=227 and 197 u were detected, it would indicate that TNT was present in the SPME extraction. If these ions were absent, but ions with m/e=182, 167, and 151 u were detected then an isomer of DNT was present.

Table 1 shows the sensitivity for trace species detection in air using a mass spectrometry method and apparatus.

TABLE 1

CURRENT VALUES FOR TARGET MOLECULE DETECTION IN AIR

| Trace Compound | Vapor Concentration (from 760 torr Air) | Measured Signal (counts/sec) |
| --- | --- | --- |
| Sulphur Hexafluoride | 1 pptr | 1,000 |
| Carbon Tetrachloride | 1 pptr | >10,000 |
| 2.4 DNT | 184 ppb | 46,000 |
| 2.4.6 TNT | 13 ppb | 7,000 |
| PETN | 26 pptr | 300 |
| RDX | 8 pptr | 100 |

Conditions:
Clock Rate = 8 kHz
Electron Current = 600 µA
Single Jet Separator Operation The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention. Only the embodiments of the present invention and but a few examples of its versatility are shown and described in the present disclosure. It is to be understood that the present invention is capable of use in various other combinations and environments and is capable of changes or modifications within the scope of the inventive concept as expressed herein. While the invention has been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains. Accordingly, other embodiments are within the scope of the following claims.

What is claimed is:

1. A method for generating a negative ion in a reversal region, the method comprising:
    a) providing an electron emitter comprising a non-planar electron-emitting surface for generating an electron beam comprising electrons;
    b) providing a lens stack comprising 1) an electron extractor for electrostatically focusing the emitted electrons of the electron beam along an axis to a reversal region and 2) an electrostatic mirror for neutralizing the kinetic energy of the electrons of the electron beam;
    c) determining the fields and trajectories for the electrons of the electron beam at the electrostatic mirror, wherein the trajectories of the electrons at the electrostatic mirror are calculated in an electric-field configuration at the electrostatic mirror that is matched to the geometry of the electron-emitting surface and the space charge of electrons in the electron beam is accounted for;
    d) determining the number of reflections to be made by the electron beam in the reversal region;
    e) modifying the geometry of the lens stack in light of the results obtained in c) and the results obtained in d) to provide an electron kinetic energy of 2 meV or less for the electrons of the electron beam and at least 5 reflections of the electron beam at the reversal region; and
    f) intersecting the reversal region with a target molecular gas beam comprising a target molecule, wherein electrons of the electron beam attach to the target molecule to form a negative ion.

2. The method of claim 1, wherein the target molecule is present in a liquid, air, or vapor sample.

3. The method of claim 2, wherein the sample is extracted by solid phase extraction, salting-out solvent extraction or membrane solid phase extraction.

4. The method of claim 3, wherein the sample is further processed by supersonic expansion in a jet separator prior to introduction.

5. The method of claim 1, wherein the target molecule is an explosive.

6. The method of claim 5, wherein the explosive is RDX, TNT, PETN, or EGDN, or any combination thereof or derivative thereof.

7. The method of claim 1, wherein the target molecule is a nerve agent.

8. The method of claim 7, wherein the nerve agent is Tabun (GA), Sarin (GB), Soman (GD), GE, V-agent (VX) (phosphonothioic acid, methyl-, S-(2bis (1-methylethylamino)ethyl) 0-ethyl ester) or pyridostigmine, or any combination thereof or derivative thereof.

9. The method of claim 1, wherein the target molecule is a pulmonary intoxicant.

10. The method of claim 9, wherein the pulmonary intoxicant is phosgene (CG), diphosgene (DP), chlorine or chloropicrin (PS), or any combination thereof or derivative thereof.

11. The method of claim 1, wherein the target molecule is a blister agent.

12. The method of claim 11, wherein the blister agent is sulfur mustard (H/HD) or nitrogen mustard (HN), arsenicals (lewisite (L)), or phosgene oxime (CX), or any combination thereof or derivative thereof.

13. The method of claim 1, wherein the target molecule is a drug.

14. The method of claim 13, wherein the drug is heroin or cocaine.

15. The method of claim 1, wherein the reversal region comprises a plurality of reversal planes of electrons.

16. The method of claim 1, wherein modifying the geometry of the lens stack comprises modifying a shape of an element in the lens stack.

17. The method of claim 1, wherein modifying the geometry of the lens stack comprises modifying a position of an element in the lens stack.

18. The method of claim 1, further comprising determining the geometry of the lens stack.

19. The method of claim 1, wherein determining the fields and trajectories for the electrons of the electron beam comprises determining the fields and trajectories by analytically determining the kinetic energy of electrons.

20. The method of claim 1, wherein the reversal region comprises a plurality of spherical equipotentials.

21. A method for generating low-energy electrons in a reversal region, the method comprising:
   a) providing an electron emitter comprising a non-planar electron-emitting surface for generating an electron beam comprising electrons;
   b) providing a lens stack comprising 1) an electron extractor for electrostatically focusing the emitted electrons of the electron beam along an axis to a reversal region and 2) an electrostatic mirror for neutralizing the kinetic energy of the electrons of the electron beam;
   c) determining the fields and trajectories for the electrons of the electron beam at the electrostatic mirror, wherein the paths of the electrons of the electron beam at the electrostatic mirror are calculated in an electric-field configuration at the electrostatic mirror that is matched to the geometry of the electron-emitting surface and the space charge of electrons in the electron beam is accounted for;
   d) determining the number of reflections to be made by the electron beam in the reversal region; and
   e) modifying the geometry of the lens stack in light of the results obtained in c) and the results obtained in d) to provide an electron kinetic energy of 2 meV or less for the electrons of the electron beam and at least 5 reflections of the electron beam at the reversal region.

22. An apparatus for generating low-energy electrons in a reversal region, the apparatus comprising:
   a) an electron emitter comprising a non-planar electron-emitting surface for generating an electron beam comprising electrons;
   b) a lens stack comprising 1) an electron extractor for electrostatically focusing the emitted electrons of the electron beam along an axis to a reversal region and 2) an electrostatic mirror for neutralizing the kinetic energy of the electrons of the electron beam;
   c) a means for determining the fields and trajectories for the electrons of the electron beam at the reversal region, wherein the trajectories of the electrons of the electron beam at the reversal region are calculated in an electric-field configuration at the reversal region that is matched to the geometry of the electron-emitting surface and the space charge of electrons in the electron beam is accounted for;
   d) a means for determining the number of electron beam reversals to be made in the reversal region;
   e) a means for analyzing the results obtained in c) and the results obtained in d) so that the geometry of said lens stack can be matched to the geometry of said electron emitter to thereby provide an electron kinetic energy of 2 meV or less for the electrons of the electron beam and at least 5 reflections of the electron beam at the reversal region.

23. The apparatus of claim 22 further comprising an ion extraction component in ion communication with the reversal region.

24. The apparatus of claim 23, further comprising a mass analyzer in ion communication with the extraction component.

25. The apparatus of claim 22, further comprising a means for modifying the geometry of the lens stack to match the geometry of said lens stack to the geometry of said electron emitter.

26. A chemical sensing apparatus for detecting the presence of a target molecule, the apparatus comprising:
   a) a gas phase jet separator having at least one first wall adjacent to an injection port, a second wall proximal said injection port and a third wall distal said injection port;
   b) an electron-ion optic chamber in vapor communication with the jet separator, the chamber comprising:
      1) an electron emitter comprising a non-planar electron-emitting surface to emit an electron beam;
      2) a lens stack comprising:
         i) an electron extractor for electrostatically focusing the emitted electrons of the electron beam along an axis to a reversal region; and
         ii) an electrostatic mirror for neutralizing the kinetic energy of the electrons of the electron beam;
   c) a means for determining the fields and trajectories for the electrons of the electron beam at the electrostatic mirror, wherein the trajectories of the electrons of the electron beam at the electrostatic mirror are calculated in an electric-field configuration at the electrostatic mirror that is matched to the geometry of the electron-emitting surface and the space charge of electrons in the electron beam is accounted for;
   d) a means for determining the number of reflections to be made by the electron beam in the reversal region;
   e) a means for analyzing the results obtained in c) and the results obtained in d) so that the lens stack can be modified to provide an electron kinetic energy of 2 meV or less for the electrons of the electron beam and at least 5 reflections of the electron beam at the reversal region;
   f) an ion extraction component in ion communication with the reversal region; and
   g) a mass analyzer in ion communication with the extraction component,
   wherein electrons of the electron beam can attach to the target molecule to generate a detectable negative ion.

27. The apparatus of claim 26, wherein the jet injector is made of stainless steel.

28. The apparatus of claim 26, wherein the jet injector further comprises a heating element.

29. The apparatus of claim 28, wherein the heating element maintains the jet injector at 140 C.

30. The apparatus of claim 26, wherein the mass analyzer is a quadrupole mass analyzer.

31. The apparatus of claim 26, wherein the optic chamber, ion extraction component and mass analyzer are contained in a vacuum chamber.

32. The apparatus of claim 26, further comprising a means for modifying a shape of an element in the lens stack.

33. The apparatus of claim 26, further comprising a means for modifying a position of an element in the lens stack.

* * * * *